US 6,532,462 B2

(12) United States Patent
Balaban

(10) Patent No.: US 6,532,462 B2
(45) Date of Patent: Mar. 11, 2003

(54) GENE EXPRESSION AND EVALUATION SYSTEM USING A FILTER TABLE WITH A GENE EXPRESSION DATABASE

(75) Inventor: David J. Balaban, San Rafael, CA (US)

(73) Assignee: Affymetrix, Inc., Santa Clara, CA (US)

( * ) Notice: Subject to any disclaimer, the term of this patent is extended or adjusted under 35 U.S.C. 154(b) by 0 days.

(21) Appl. No.: 09/940,285

(22) Filed: Aug. 27, 2001

(65) Prior Publication Data

US 2002/0062319 A1 May 23, 2002

Related U.S. Application Data

(63) Continuation of application No. 09/122,434, filed on Jul. 24, 1998, now Pat. No. 6,308,170.
(60) Provisional application No. 60/069,198, filed on Dec. 11, 1997, provisional application No. 60/069,436, filed on Dec. 11, 1997, and provisional application No. 60/053,842, filed on Jul. 25, 1997.

(51) Int. Cl.[7] .......................... G06F 17/30; G06F 19/00
(52) U.S. Cl. ............................................... 707/4; 702/19
(58) Field of Search ................. 435/6; 702/19, 702/20; 707/3, 4, 5, 6, 104

(56) References Cited

U.S. PATENT DOCUMENTS

| | | | |
|---|---|---|---|
| 4,683,202 A | 7/1987 | Mullis | 435/6 |
| 5,143,854 A | 9/1992 | Pirrung et al. | 436/518 |
| 5,206,137 A | 4/1993 | Ip et al. | 435/6 |
| 5,445,934 A | 8/1995 | Fodor et al. | 435/6 |
| 5,492,806 A | 2/1996 | Drmanac et al. | 435/5 |

(List continued on next page.)

FOREIGN PATENT DOCUMENTS

| | | |
|---|---|---|
| EP | 0 307 476 | 3/1989 |
| EP | 0 235 726 | 5/1989 |
| EP | 0 392 546 | 10/1990 |
| EP | 0 717 113 | 7/1996 |
| EP | 0 848 067 | 6/1998 |

(List continued on next page.)

OTHER PUBLICATIONS

U.S. patent application Ser. No. 08/828,952, Webster et al., filed Mar. 28, 1997.
Okubo et al., "Large Scale cDNA Sequencing for Analysis of Quantitative and Qualitative Aspects of Gene Expression", Nature Genetics, 2(3):173–179 (1993).
IntelliGenetics Suite (TM), Release 5.4, Advanced Training Manual, Jan. 1993, published by IntelliGenetics Inc., 700 East El Camino Real, Mountain View, California 94040, USA, pp. (1–6)–(1–19) and (2–9)–(2–14), see entire document.

(List continued on next page.)

Primary Examiner—Jack Choules
(74) Attorney, Agent, or Firm—Charles J. Kulas; Townsend and Townsend and Crew LLP

(57) ABSTRACT

A filter table provides a framework in which queries are efficiently and easily developed to access a gene expression database. The filter table is used to filter a plurality of expression levels to return a reduced set of expression levels, which may be further queried to provide more specific results. Using the filtering and querying provided one can easily identify genes or expressed sequence tags whose expression correlates to particular tissue types. Various tissue types may correspond to different diseases, states of disease progression, different organs, different species, etc. Researchers may now use large-scale gene expression databases to full advantage.

20 Claims, 15 Drawing Sheets

U.S. PATENT DOCUMENTS

| | | | |
|---|---|---|---|
| 5,525,464 A | | 6/1996 | Drmanac et al. ............... 435/6 |
| 5,530,177 A | * | 6/1996 | Bleck et al. ................... 800/7 |
| 5,571,639 A | | 11/1996 | Hubbell et al. ................ 435/5 |
| 5,593,839 A | | 1/1997 | Hubbell et al. ................ 435/6 |
| 5,667,972 A | | 9/1997 | Drmanac et al. ............... 435/6 |
| 5,695,940 A | | 12/1997 | Drmanac et al. ............... 435/6 |
| 5,700,637 A | | 12/1997 | Southern ....................... 435/6 |
| 5,707,806 A | | 1/1998 | Shuber .................... 435/287.1 |
| 5,777,888 A | | 7/1998 | Rine et al. ..................... 703/19 |
| 5,843,767 A | | 12/1998 | Beattie ....................... 382/129 |
| 5,871,697 A | | 2/1999 | Rothberg et al. |
| 5,968,784 A | * | 10/1999 | Spinella et al. ............ 435/91.1 |
| 5,974,164 A | | 10/1999 | Chee et al. ................ 435/91.2 |
| 6,025,194 A | * | 2/2000 | Funk ....................... 435/320.1 |
| 6,096,503 A | * | 8/2000 | Sutcliffe et al. ............... 435/6 |

FOREIGN PATENT DOCUMENTS

| | | |
|---|---|---|
| WO | WO 89/11548 | 11/1989 |
| WO | WO 90/15070 | 12/1990 |
| WO | WO 92/10092 | 6/1992 |
| WO | WO 92/10588 | 6/1992 |
| WO | WO 93/22456 | 11/1993 |
| WO | WO 95/11995 | 5/1995 |
| WO | WO 96/23078 | 8/1996 |
| WO | WO 97/10365 | 3/1997 |
| WO | WO 97/17317 | 5/1997 |
| WO | WO 97/19410 | 5/1997 |
| WO | WO 97/27317 | 7/1997 |
| WO | WO 97/29212 | 8/1997 |

OTHER PUBLICATIONS

Drmanac, "Sequencing of Megabase Plus DNA by Hybridization: Theory of the Method", *Genomics*, 4:114–128 (1989).

Gibbs et al., "Detection of Single DNA Base Differences by Competitive Oligonucleotide Priming", *Nucleic Acid Res.*, 17(7):2437–2448 (1989).

Guatelli et al., "Isothermal, In Vitro Amplification of Nucleic Acids by a Multienzyme Reaction Modeled After Retroviral Replication", *Proc. Natl. Acad. Sci. USA*, 87(5):1874–1878 (1990).

Gusella, "DNA Polymorphism and Human Disease", *Annu. Rev. Biochem.*, 55:831–854 (1986).

Kwoh et al., "Transcription–Based Amplification System and Detection of Amplified Human Immunodeficiency Virus Type 1 With a Bead–Based Sandwich Hybridization Format", *Proc. Natl. Acad. Sci. USA*, 86(4):1173–1177 (1989).

Landegren et al., "A Ligase–Mediated Gene Detection Technique", *Science*, 241(4869):1077–1080 (1988).

Mattila et al., "Fidelity of DNA Synthesis by the Thermococcus litoralis DNA Polymerase—An Extremely Heat Stable Enzyme With Proofreading Activity", *Nucleic Acid Res.*, 19(18):4967–4973 (1991).

Orita et al., "Detection of Polymorphisms of Human DNA by Gel Electrophoresis as Single–Strand Conformation Polymorphisms", *Proc. Natl. Acad. Sci. USA*, 86(8):2766–2770 (1989).

Saiki et al., "Analysis of Enzymatically Amplified Beta–Globin and HLA–DQ Alpha DNA with Allele–Specific Oligonucleotide Probes", *Nature*, 324(6093)163–166 (1986).

Wu et al., "The Ligation Amplification Reaction (LAR)—Amplification of Specific DNA Sequences Using Sequential Rounds of Template–Dependent Ligation", *Genomics*, 4(4):560–569 (1989).

Zhao et al., "High–density cDNA filter analysis: a novel approach for large-scale, quantitative analysis of gene expression," *Gene*, 156:207–213 (1995).

Adams et al., "Complementary DNA Sequencing: Expressed Sequence Tags and Human Genome Project", *Science*, 252(5013):1651–1656 (1991).

Frickett et al., "Development Of A Database For Nucleotide Sequences", *Mathematical Methods for DNA Sequences*, CRC Press, Ed. Waterman, pp. 2–34 (1989).

Hara et al., "Subtractive cDNA Cloning Using Oligo(dT)$_{30}$–Latex And PCR: Isolation Of cDNA Clones Specific To Undifferentiated Human Embryonal Carcinoma Cells", *Nucleic Acids Res.*, 19(25):7097–7104 (1991).

Khan et al., "Single Pass Sequencing And Physical And Genetic Mapping Of Human Brain cDNAs", *Nat. Genet.*, 2(3):180–185 (1992).

Matsubara et al., "Identification Of New Genes By Systematic Analysis Of cDNAs And Database Construction", *Curr. Opin. Biotechnol.*, 4(6):672–677 (1993).

PR Newswire, "Gene Logic to Use Affymetrix GeneChip Arrays to Build Gene Expression Database Products", Jan. 11, 1999.

PR Newswire, "Gene Logic to USe Affymetrix GeneChip Arrays to Build Gene Expression Database Products," Jan. 11, 1999.

Adams et al., "Complementary DNA Sequencing: Expressed Sequence Tags and Human Genome Project," *Science*, 252(5013):1651–1656 (1991).

Drmanac, "Sequencing of Megabase Plus DNA by Hybridization: Theory of the Method," *Genomics*, 4:114–128 (1989).

Frickett et al., "Development Of A Database For Nucleotide Sequences," from *Mathematical Methods for DNA Sequences*, CRC Press, Ed. Waterman, pp. 2–34 (1989).

Gibbs et al., "Detection of Single DNA Base Differences by Competitive Oligonucleotide Priming," *Nuc. Acids Res.*, 17(7):2437–2448 (1989).

Guatelli et al., "Isothermal, In Vitro amplification of Nucleic Acids by a Multienzyme Reaction Modeled After Retroviral Replication," *PNAS*, 87(5):1874–1878 (1990).

Gusella, "DNA Polymorphism and Human Disease," *Annu. Rev. Biochem.*, 55:831–854 (1986).

Hara et al., "Subtractive cDNA Cloning Using Oligo(dT).sub.30–Latex And PCR: Isolation Of cDNA Clones Specific To Undifferentiated Human Embryonal Carcinoma Cells," *Nuc. Acids Res.*, 19(25):7097–7104 (1991).

IntelliGenetics Suite ™, Release 5.4, Advanced Training Manual, Jan. 1993, published by IntelliGenetics, Inc., 700 East El Camino Real, Mountain View, CA 94040, USA, pp. (1–6)–(1–19) and (2–9)–(2–14).

Kahn et al., "Single Pass Sequencing And Physical And Genetic Mapping Of Human Brain cDNAs," *Nat. Genet.*, 2(3):180–185 (1992).

Kwoh et al., "Transcription–Based Amplification System and Detection of Amplified Human Immunodeficiency Virus Type 1 With a Bead–Based Sandwich Hybridization Format," *PNAS*, 86(4):1173–1177 (1989).

Landegren et al., "A Ligase–Mediated Gene Detection Technique," *Science*, 241(4869):1077–1080 (1988).

Matsubara et al., "Identification Of New Genes By Systematic Analysis Of cDNAs And Database Construction," *Curr. Opin. Biotechnol.*, 4(6):672–677 (1993).

Mattila et al., "Fidelity of DNA synthesis by the Thermoccus litoralis DNA Polymerase—An Extremely Heat Stable Enzyme With Proofreading Activity," *Nuc. Acids. Res.*, 19(18):4967–4973 (1991).

* cited by examiner

FIG. 5B filter experiments

| Experiment Na | Gene Name | Positive | Negative | Pairs | Pairs Used | Pairs InAvg | Pos Fra |
|---|---|---|---|---|---|---|---|

[ delete filter ]

[ filter ] [ reset filter ] [ save filter ] [ export ] [ close ]

534

| Experiment Na | Gene Name | Positive | Negative | Pairs | Pairs Used | Pairs InAvg | Pos F |
|---|---|---|---|---|---|---|---|
| sy050103 | 100M95678 | 8.00 | 3.00 | 20.00 | 20.00 | 18.00 | |
| sy080501 | 100M95678 | 12.00 | 1.00 | 20.00 | 20.00 | 18.00 | |
| sy052001 | 100M95678 | 8.00 | 2.00 | 20.00 | 20.00 | 18.00 | |
| sy071501 | 100M95678 | 12.00 | 2.00 | 20.00 | 20.00 | 18.00 | |
| sy062001 | 100M95678 | 10.00 | 0.00 | 20.00 | 20.00 | 17.00 | |
| sy080503 | 100M95678 | 11.00 | 1.00 | 20.00 | 20.00 | 18.00 | |

Record  1  of 89748

Pivot Value: FixedAvgDiff

- AffyID
- AvgDiff
- FixedAvgDiff
- LogAvg
- MM Excess

548

Pivot Column:

[ pivot ]

FIG. 5F

GENE EXPRESSION AND EVALUATION SYSTEM USING A FILTER TABLE WITH A GENE EXPRESSION DATABASE

CROSS-REFERENCE TO RELATED APPLICATIONS

The present application is a continuation of U.S. application Ser. No. 09/122,434 filed Jul. 24, 1998 now U.S. Pat. No. 6,308,170, which claims priority from U.S. Prov. App. No. 60/053,842 filed Jul. 25, 1997, entitled COMPREHENSIVE BIO-INFORMATICS DATABASE, from U.S. Prov. App. No. 60/069,198 filed on Dec. 11, 1997, entitled COMPREHENSIVE DATABASE FOR BIOINFORMATICS, and from U.S. Prov. App. No. 60/069,436, entitled GENE EXPRESSION AND EVALUATION SYSTEM, filed on Dec. 11, 1997. The contents of all three provisional applications are herein incorporated by reference.

The subject matter of the present application is related to the subject matter of the following three co-assigned applications filed on the same day as the present application: METHOD AND APPARATUS FOR PROVIDING A BIO-INFORMATICS DATABASE Ser. No. 09/122,167 now U.S. Pat. No. 6,229,911, METHOD AND SYSTEM FOR PROVIDING A POLYMORPHISM DATABASE Ser. No. 09/122,169, METHOD AND SYSTEM FOR PROVIDING A PROBE ARRAY CHIP DESIGN DATABASE Ser. No. 09/122,304 now U.S. Pat. No. 6,188,783. The contents of these three applications are herein incorporated by reference.

BACKGROUND OF THE INVENTION

The present invention relates to computer systems and more particularly to computer systems for analyzing expression levels or concentrations.

Devices and computer systems have been developed for collecting information about gene expression or expressed sequence tag (EST) expression in large numbers of tissue samples. For example, PCT application WO92/10588, incorporated herein by reference for all purposes, describes techniques for sequencing or sequence checking nucleic acids and other materials. Probes for performing these operations may be formed in arrays according to the methods of, for example, the pioneering techniques disclosed in U.S. Pat. Nos. 5,143,854 and 5,571,639, both incorporated herein by reference for all purposes.

According to one aspect of the techniques described therein, an array of nucleic acid probes is fabricated at known locations on a chip or substrate. A fluorescently labeled nucleic acid is then brought into contact with the chip and a scanner generates an image file indicating the locations where the labeled nucleic acids bound to the chip. Based upon the identities of the probes at these locations, it becomes possible to extract information such as the monomer sequence of DNA or RNA.

Computer-aided techniques for monitoring gene expression using such arrays of probes have been developed as disclosed in EP Pub. No. 0848067 and PCT publication No. WO 97/10365, the contents of which are herein incorporated by reference. Many disease states are characterized by differences in the expression levels of various genes either through changes in the copy number of the genetic DNA or through changes in levels of transcription (e.g., through control of initiation, provision of RNA precursors, RNA processing, etc.) of particular genes. For example, losses and gains of genetic material play an important role in malignant transformation and progression. Furthermore, changes in the expression (transcription) levels of particular genes (e.g., oncogenes or tumor suppressors), serve as signposts for the presence and progression of various cancers.

Information on expression of genes or expressed sequence tags may be collected on a large scale in many ways, including the probe array techniques described above. One of the objectives in collecting this information is the identification of genes or ESTs whose expression is of particular importance. Researchers wish to answer questions such as: 1) Which genes are expressed in cells of a malignant tumor but not expressed in either healthy tissue or tissue treated according to a particular regime? 2) Which genes or ESTs are expressed in particular organs but not in others? 3) Which genes or ESTs are expressed in particular species but not in others?.

Collecting vast amounts of expression data from large numbers of samples including all the tissue types mentioned above is but the first step in answering these questions. To derive full value from the investment made in collecting and storing expression data, one must be able to efficiently mine the data to find items of particular relevance. What is needed is an efficient and easy to use query system for a gene expression database.

SUMMARY OF THE INVENTION

An efficient and easy to use query system for a gene expression database is provided by virtue of the present invention. Using such a system, one can easily identify genes or expressed sequence tags whose expression correlates to particular tissue types. Various tissue types may correspond to different diseases, states of disease progression, different organs, different species, etc. Researchers may now use large scale gene expression databases to full advantage.

According to a first aspect of the present invention, a method is provided in a computer system for operating a database storing information about compound concentration. The method includes: providing a database including concentrations of a plurality of compounds as measured in a plurality of samples, accepting a user query to the database to identify desired ones of the plurality of compounds, the user query specifying concentration characteristics of the desired compounds in selected ones of the plurality of samples, and comparing the concentration characteristics to the concentrations stored in the database to identify the desired compounds.

A further understanding of the nature and advantages of the inventions herein may be realized by reference to the remaining portions of the specification and the attached drawings.

BRIEF DESCRIPTION OF THE DRAWINGS

FIGS. 5A–5L depict a user interface for querying an expression database according to one embodiment of the present invention.

DESCRIPTION OF SPECIFIC EMBODIMENTS

Figure 1:
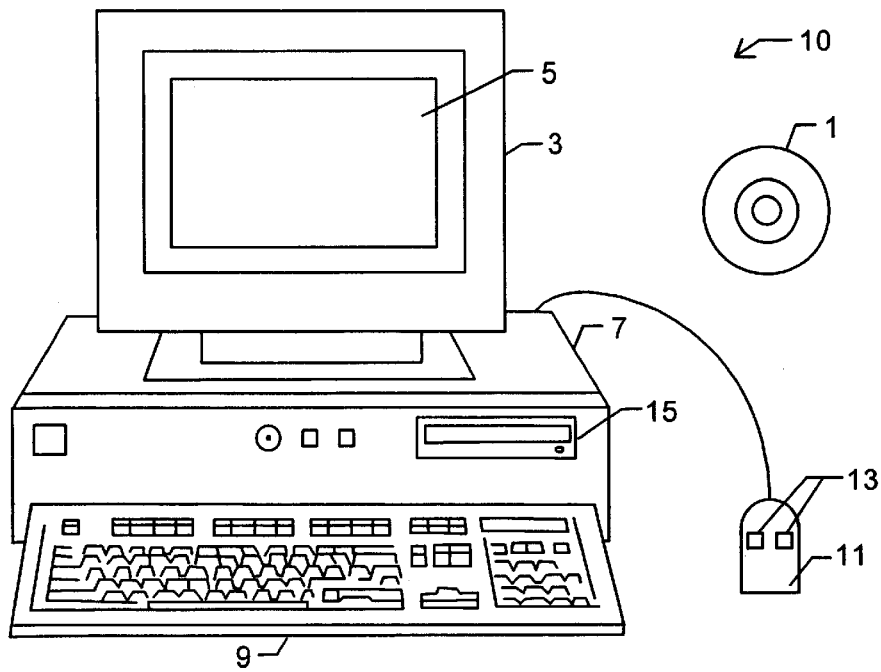
FIG. 1 illustrates an example of a computer system that may be used to execute software embodiments of the present invention.

FIG. 1 illustrates an example of a computer system that may be used to execute software embodiments of the present invention. FIG. 1 shows a computer system 1 which includes a monitor 3, screen 5, cabinet 7, keyboard 9, and mouse 11. Mouse 11 may have one or more buttons such as mouse buttons 13. Cabinet 7 houses a CD-ROM drive 15 and a hard drive (not shown) that may be utilized to store and retrieve software programs including computer code incorporating the present invention. Although a CD-ROM 17 is shown as the computer readable medium, other computer readable media including floppy disks, DRAM, hard drives, flash memory, tape, and the like may be utilized. Cabinet 7 also houses familiar computer components (not shown) such as a processor, memory, and the like.

Figure 2:
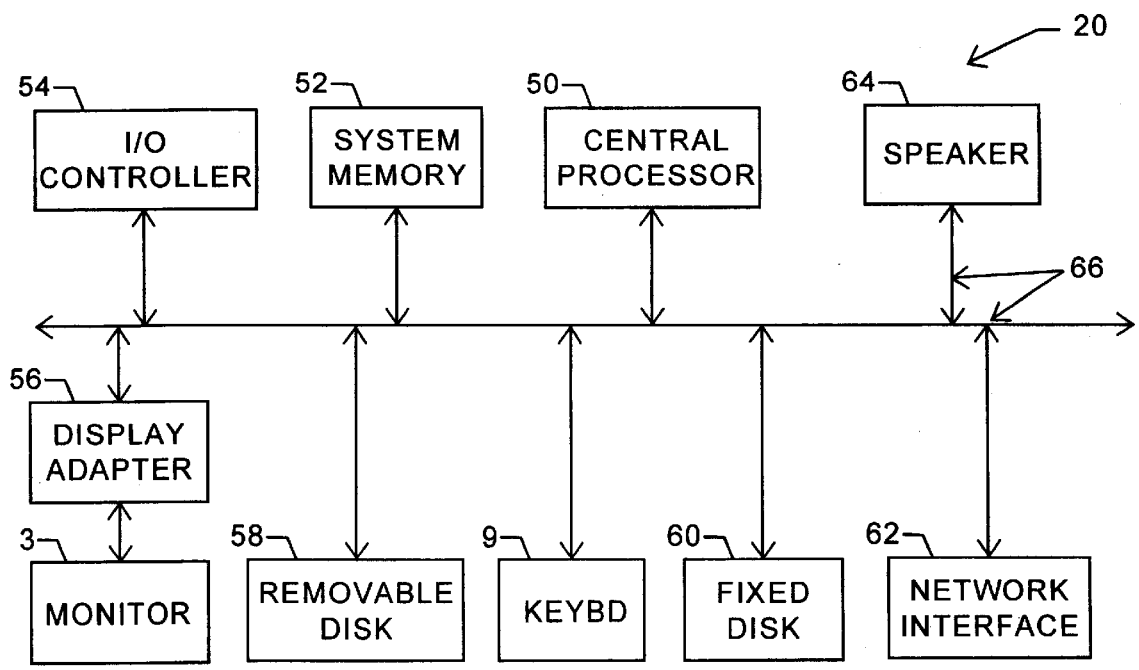
FIG. 2 shows a system block diagram of a typical computer system.

FIG. 2 shows a system block diagram of computer system 1 used to execute software embodiments of the present invention. As in FIG. 1, computer system 1 includes monitor 3 and keyboard 9. Computer system 1 further includes subsystems such as a central processor 50, system memory 52, I/O controller 54, display adapter 56, removable disk 58, fixed disk 60, network interface 62, and speaker 64. Removable disk 58 is representative of removable computer readable media like floppies, tape, CD-ROM, removable hard drive, flash memory, and the like. Fixed disk 60 is representative of an internal hard drive or the like. Other computer systems suitable for use with the present invention may include additional or fewer subsystems. For example, another computer system could include more than one processor 50 (i.e., a multi-processor system) or memory cache.

Arrows such as 66 represent the system bus architecture of computer system 1. However, these arrows are illustrative of any interconnection scheme serving to link the subsystems. For example, display adapter 56 may be connected to central processor 50 through a local bus or the system may include a memory cache. Computer system 1 shown in FIG. 2 is but an example of a computer system suitable for use with the present invention. Other configurations of subsystems suitable for use with the present invention will be readily apparent to one of ordinary skill in the art. In one embodiment, the computer system is an IBM compatible personal computer.

The VLSIPS™ and GeneChip™ technologies provide methods of making and using very large arrays of polymers, such as nucleic acids, on very small chips. See U.S. Pat. No. 5,143,854 and PCT Patent Publication Nos. WO 90/15070 and 92/10092, each of which is hereby incorporated by reference for all purposes. Nucleic acid probes on the chip are used to detect complementary nucleic acid sequences in a sample nucleic acid of interest (the "target" nucleic acid).

It should be understood that the probes need not be nucleic acid probes but may also be other polymers such as peptides. Peptide probes may be used to detect the concentration of peptides, polypeptides, or polymers in a sample. The probes should be carefully selected to have bonding affinity to the compound whose concentration they are to be used to measure.

In one embodiment, the present invention provides methods of reviewing and analyzing information relating to the concentration of compounds in a sample as measured by monitoring affinity of the compounds to polymers such as polymer probes. In a particular application, the concentration information is generated by analysis of hybridization intensity files for a chip containing hybridized nucleic acid probes. The hybridization of a nucleic acid sample to certain probes may represent the expression level of one more genes or expressed sequence tags (EST). The expression level of a gene or EST is herein understood to be the concentration within a sample of mRNA or protein that would result from the transcription of the gene or EST.

Expression level information that is reviewed and/or analyzed by virtue of the present invention need not be obtained from probes but may originate from any source. If the expression information is collected from a probe array, the probe array need not meet any particular criteria for size and density. Furthermore, the present invention is not limited to reviewing and/or analyzing fluorescent measurements of bondings such as hybridizations but may be readily utilized for reviewing and/or analyzing other measurements.

Concentration of compounds other than nucleic acids may be reviewed and/or analyzed according to one embodiment of the present invention. For example, a probe array may include peptide probes which may be exposed to protein samples, polypeptide samples, or peptide samples which may or may not bond to the peptide probes. By appropriate selection of the peptide probes, one may detect the presence or absence of particular proteins, polypeptides, or peptides which would bond to the peptide probes.

A system that designs a chip mask, synthesizes the probes on the chip, labels nucleic acids from a target sample, and scans the hybridized probes is set forth in U.S. Pat. No. 5,571,639 which is hereby incorporated by reference for all purposes. However, the present invention may be used separately for reviewing and/or analyzing the results of other systems for generating expression information, or for reviewing and/or analyzing concentrations of polymers other than nucleic acids.

The term "perfect match probe" refers to a probe that has a sequence that is perfectly complementary to a particular target sequence. The test probe is typically perfectly complementary to a portion (subsequence) of the target sequence. The term "mismatch control" or "mismatch probe" refer to probes whose sequence is deliberately selected not to be perfectly complementary to a particular target sequence. For each mismatch (MM) control in an array there typically exists a corresponding perfect match (PM) probe that is perfectly complementary to the same particular target sequence.

Among the important pieces of information obtained from the chips are the relative fluorescent intensities obtained from the perfect match probes and mismatch probes. These intensity levels are used to estimate an expression level for a gene or EST. The computer system used for analysis will preferably have available other details of the experiment including possibly the gene name, gene sequence, probe sequences, probe locations on the substrate, and the like.

Figure 3:
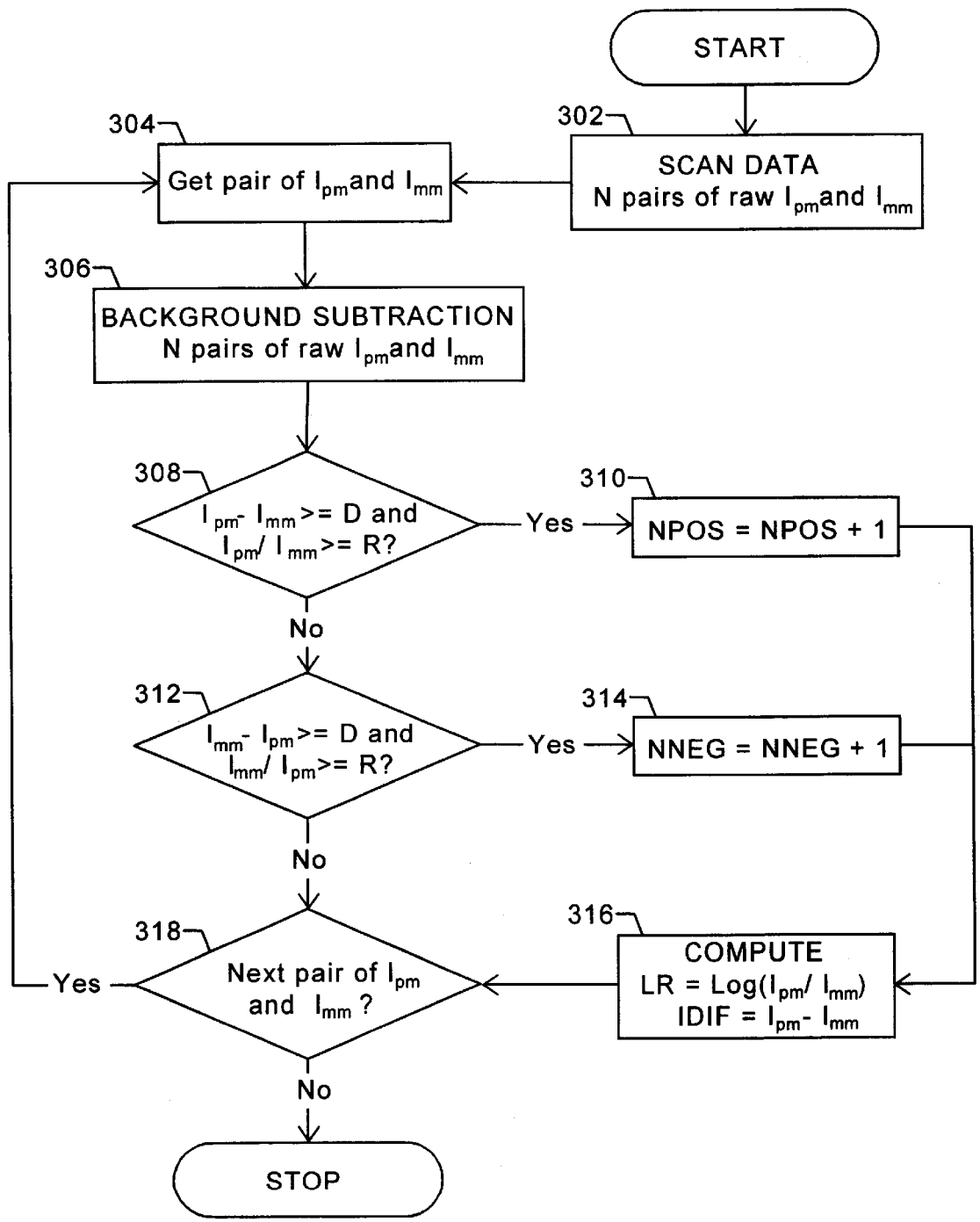
FIG. 3 is a flowchart describing steps of developing expression data according to one embodiment of the present invention.

An expression analysis is performed for each gene for each experiment. FIG. 3 is a flowchart describing steps of estimating an expression level for a particular gene as measured in a particular experiment on a chip. At step 302, the computer system receives raw scan data of N pairs of perfect match and mismatch probes. In a preferred embodiment, the hybridization intensities are photon counts from a fluorescein labeled target that has hybridized to the probes on the substrate. For simplicity, the hybridization intensity of a perfect match probe will be designed "$I_{pm}$" and the hybridization intensity of a mismatch probe will be designed "$I_{mm}$."

Hybridization intensities for a pair of probes are retrieved at step 304. The background signal intensity is subtracted from each of the hybridization intensities of the pair at step 306. Background subtraction can also be performed on all the raw scan data at the same time.

At step 308, the hybridization intensities of the pair of probes are compared to a difference threshold (D) and a ratio threshold (R). It is determined if the difference between the hybridization intensities of the pair ($I_{pm}-I_{mm}$) is greater than or equal to the difference threshold AND the quotient of the hybridization intensities of the pair ($I_{pm}/I_{mm}$) is greater than or equal to the ratio threshold. The difference thresholds are typically user defined values that have been determined to produce accurate expression monitoring of a gene or genes. In one embodiment, the difference threshold is 20 and the ratio threshold is 1.2.

If $I_{pm}-I_{mm}>=D$ and $I_{pm}/I_{mm}>=R$, the value NPOS is incremented at step 310. In general, NPOS is a value that indicates the number of pairs of probes which have hybridization intensities indicating that the gene is likely expressed. NPOS is utilized in a determination of the expression of the gene.

At step 312, it is determined if $I_{mm}-I_{pm}>=D$ and $I_{mm}/I_{pm}>=R$. If these expressions are true, the value NNEG is incremented at step 314. In general, NNEG is a value that indicates the number of pairs of probes which have hybridization intensities indicating that the gene is likely not expressed. NNEG, like NPOS, is utilized in a determination of the expression of the gene.

For each pair that exhibits hybridization intensities either indicating the gene is expressed or not expressed, a log ratio value (LR) and intensity difference value (IDIF) are calculated at step 316. LR is calculated by the log of the quotient of the hybridization intensities of the pair ($I_{pm}/I_{mm}$). The IDIF is calculated by the difference between the hybridization intensities of the pair ($I_{pm}-I_{mm}$). If there is a next pair of hybridization intensities at step 318, they are retrieved at step 304.

For each analysis performed certain data is stored in an expression analysis database. There is preferably a record for each gene or EST for which the chip measures expression. This record includes fields to hold various pieces of information. One field stores an analysis ID to identify the analysis. A result type ID field indicates whether the listed expression results indicate that the gene is present, marginal, absent, or unknown based on application of a decision matrix to the values P1, P2, P3, and P4. A number_positive field shows NPOS. An number_negative field shows NNEG. A number_used field shows the number of probes belonging to pairs that incremented NNEG or NPOS. A number_all field indicates N. An average log ratio field indicates the average LR for all probe pairs. A number_ positive_exceeds field indicates the value of NPOS−NNEG. A number_negative_exceeds field indicates the value of NNEG−NPOS. An average differential intensity field indicates the average IDIF for the probe pairs. A number_in_ average field indicates the number of probe pairs used in computing the average.

Figure 4:
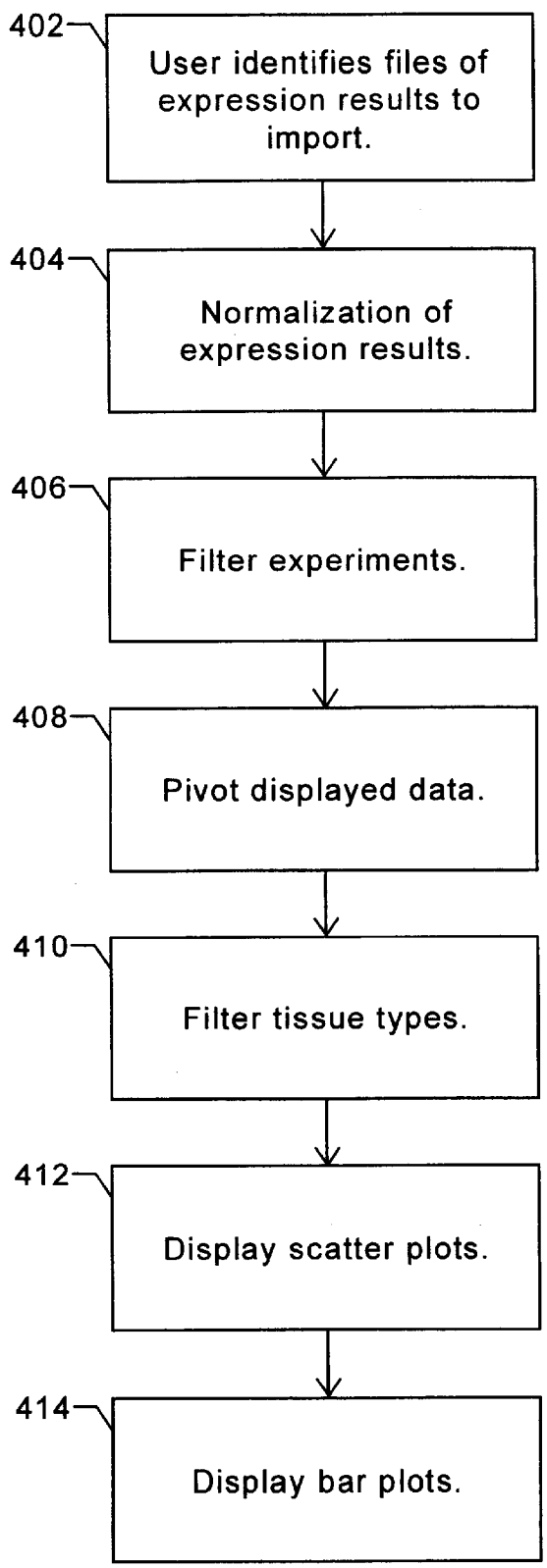
FIG. 4 is a flowchart describing steps of querying an expression database according to one embodiment of the present invention.

Steps of operating a user interface to the expression database will now be illustrated with reference to FIG. 4. The steps of FIG. 4 may be repeated or may occur in a different order, or one or more steps may be omitted. The discussion of the user interface will also refer to FIGS. 5A–5L which depict representative screen displays of the user interface.

Figure 5A:
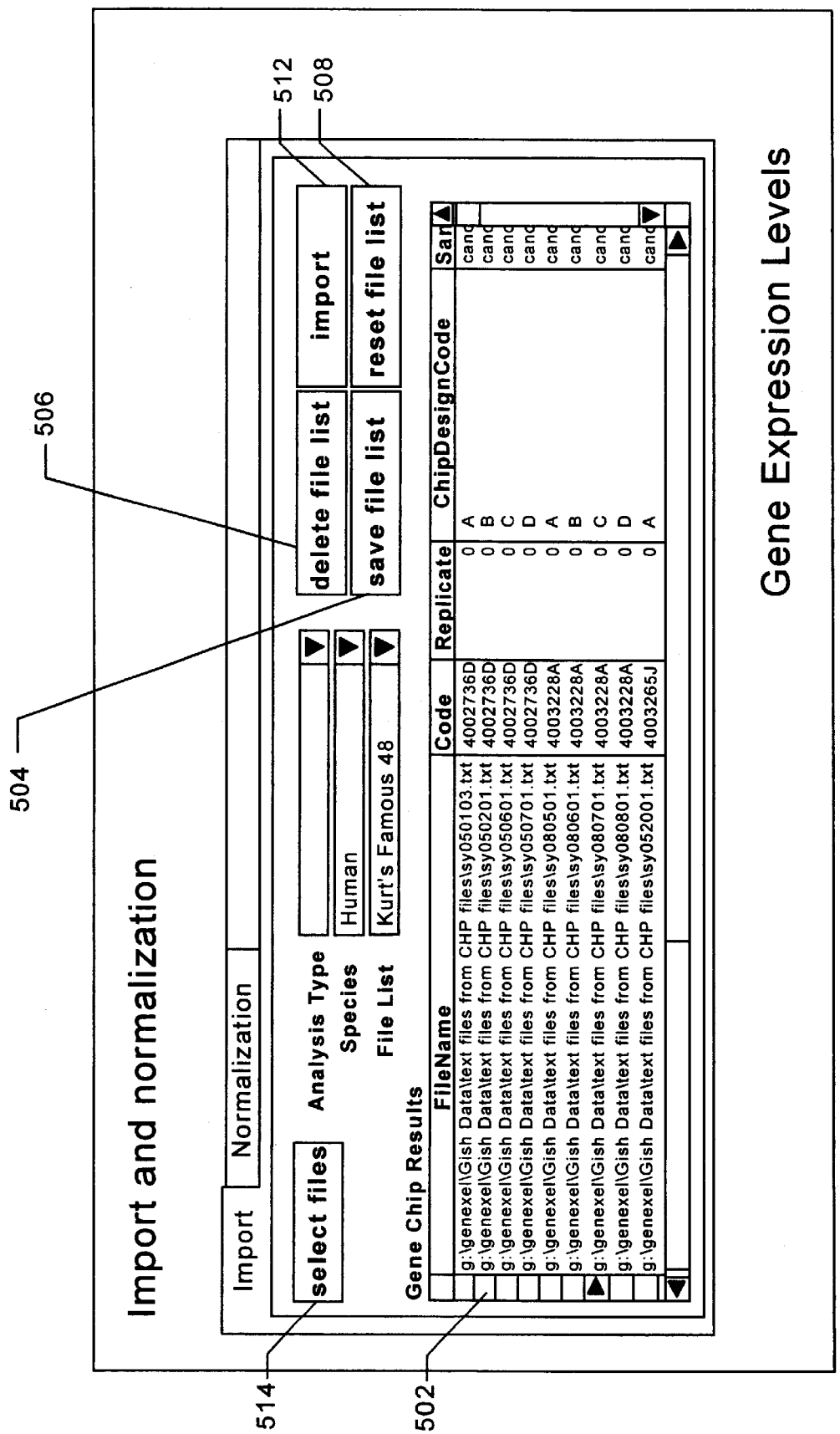

At step 402, the user selects files of expression analysis results for querying. FIG. 5A illustrates an interface screen where the user may specify expression results files. Each file represents one experiment. A table 502 lists the files that have already been selected. A given list may be saved for later use by selecting a button 504. A previously saved list may be deleted by selecting a button 506. A button 508 resets the list depicted in table 502 to a previously saved version. An import button 512 imports the contents of the files depicted in table 502 for querying. Within table 502, a file name column lists the file names that would be imported by application of import button 512. A code column indicates the tissue type for the expression data in each file. A replicate file indicates whether the file is a duplicate. A chip design code column indicates the chip design used to generate the data for the file. Various other columns (not shown) give further information about the analysis result data.

Figure 5B:
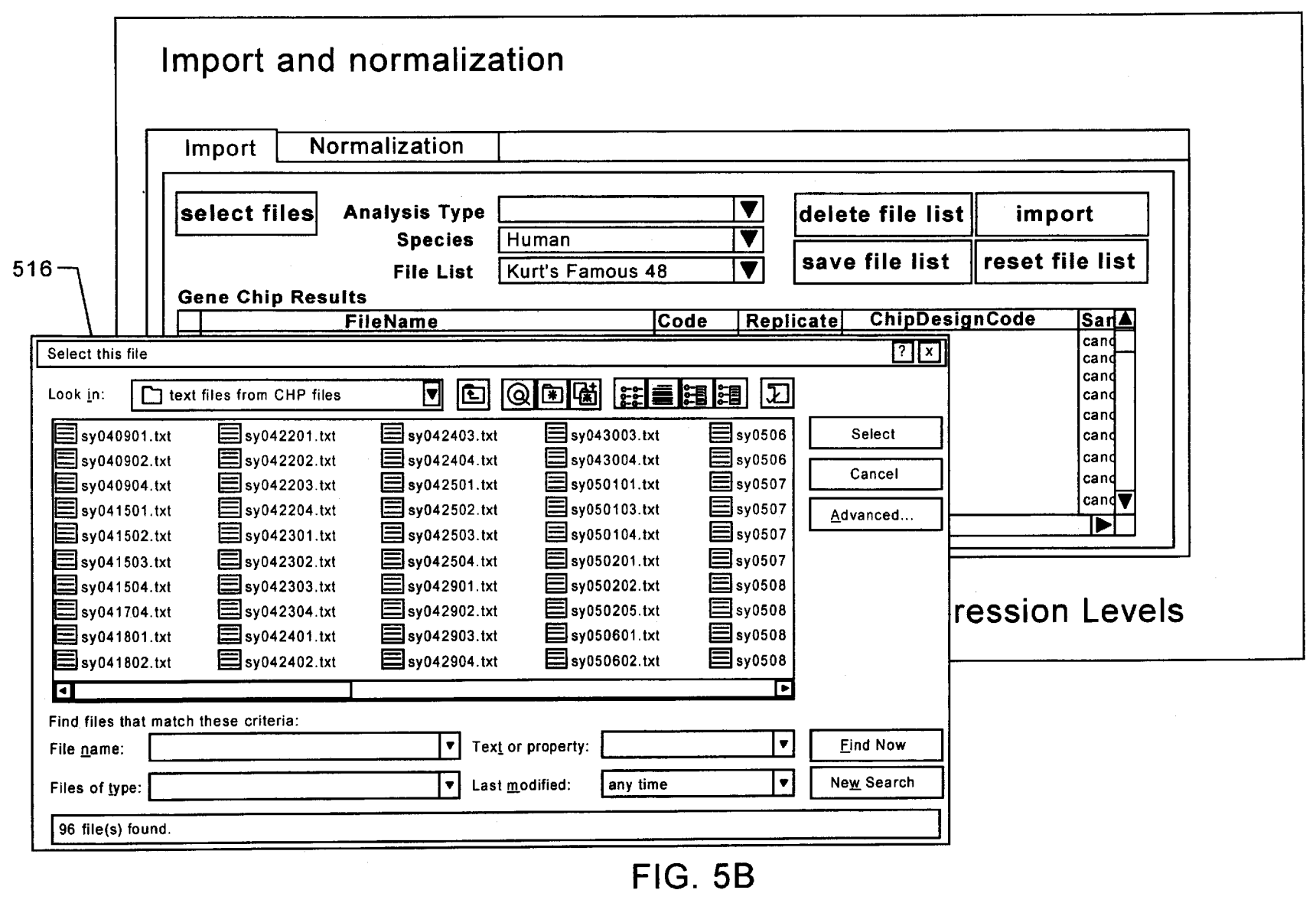
Figure 5C:
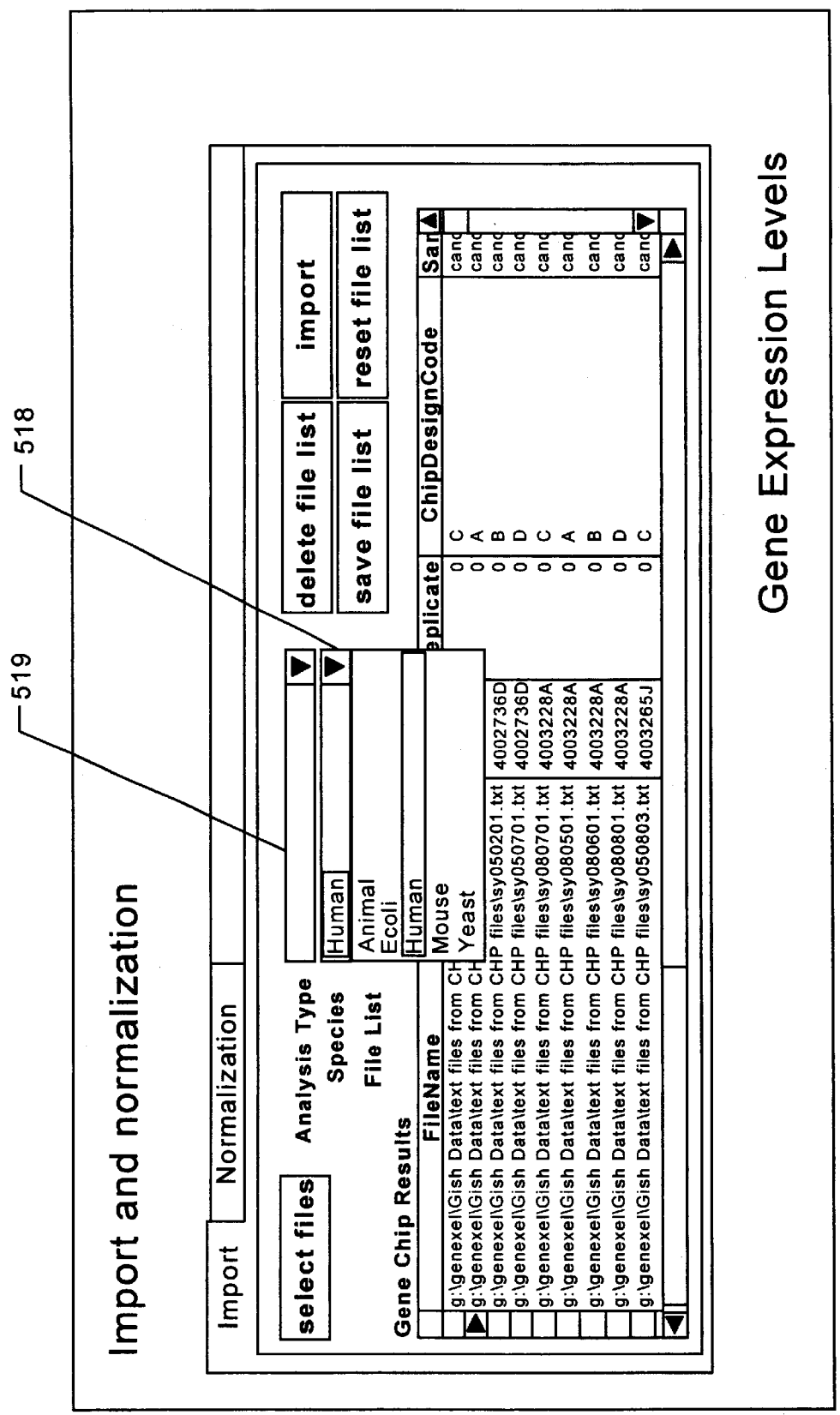

By selecting a select files button 514, the user calls up a select files screen 516 as shown in FIG. 5B. This provides an interactive file search and selection process that does not require typing in the file name. Before importing the file list, the user should select a species by using a species drop-down list 518 as shown in FIG. 5C. An analysis-type drop down list 519 allows the user to select between a relative expression analysis and an absolute expression analysis.

Figure 5D:
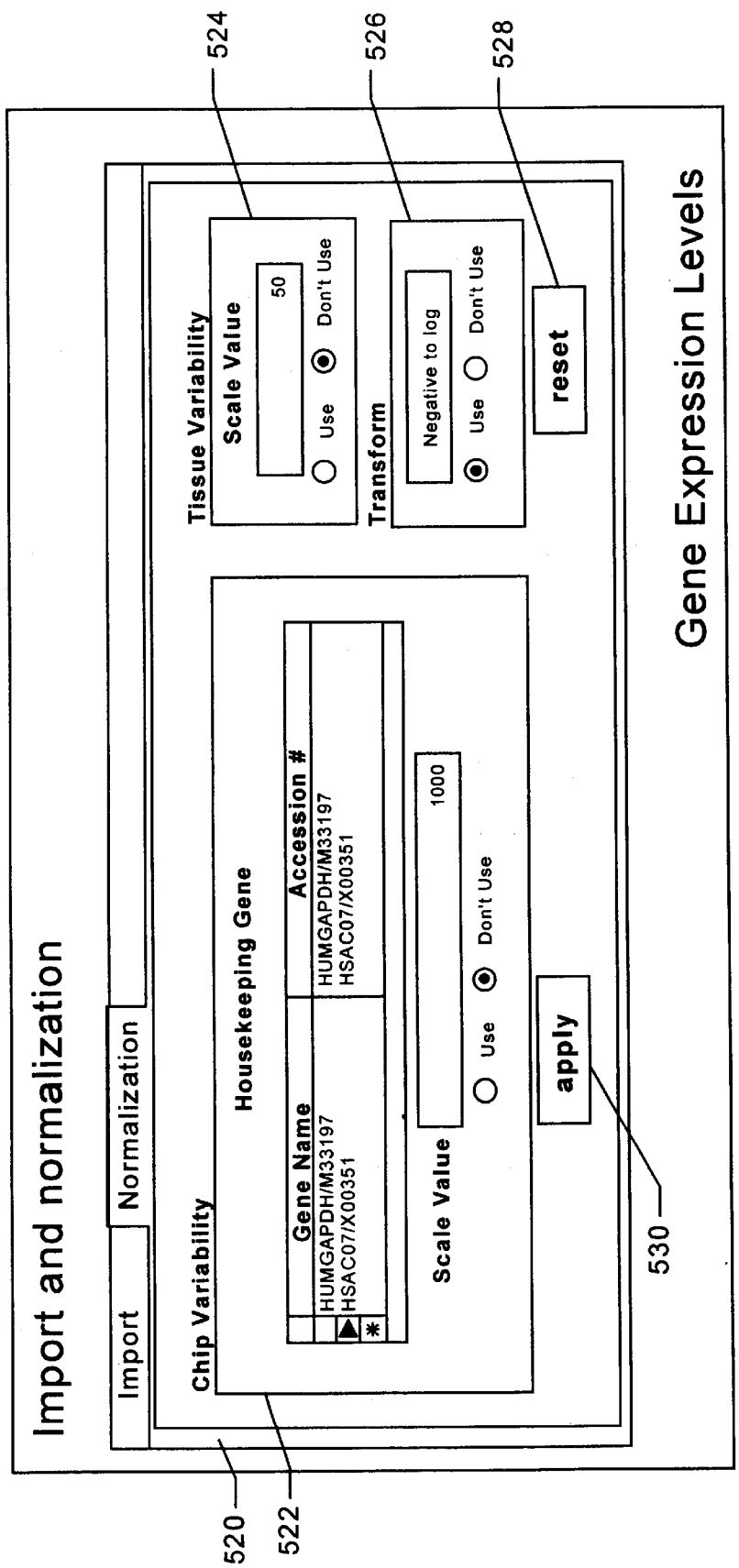

FIG. 5D shows a normalization form 520 for normalizing imported expression results at step 404. The software scales the average difference data generated by the analysis routine based on the user's selections on normalization form 520. In a chip variability area 522, the user specifies housekeeping genes with known expression levels and selects a scale value. The user can elect to either apply or not apply this scale value. If the user elects to apply the scale value, each gene expression level measured on a single chip is multiplied by a value equal to the desired scaling factor divided by the average of housekeeping expression levels measured on that chip.

Also on normalization form 520, in a tissue variability area 524, the user may select a scale value that applies to data collected from multiple chips and whether or not it is applied. If this scale value is to be applied, each expression value measured in a chip set is multiplied by a factor equal to the scale value divided by the average expression level measured over all genes for the entire chip set. A transformation area 526 allows the user to select whether negative average difference values are to be converted to positive numbers by use of a logarithmic transform. The user can reset all the changes made on normalization form 520 by selecting a reset button 528 or apply the selected normalizations and transformations by selecting an apply button 530.

Figure 5E:
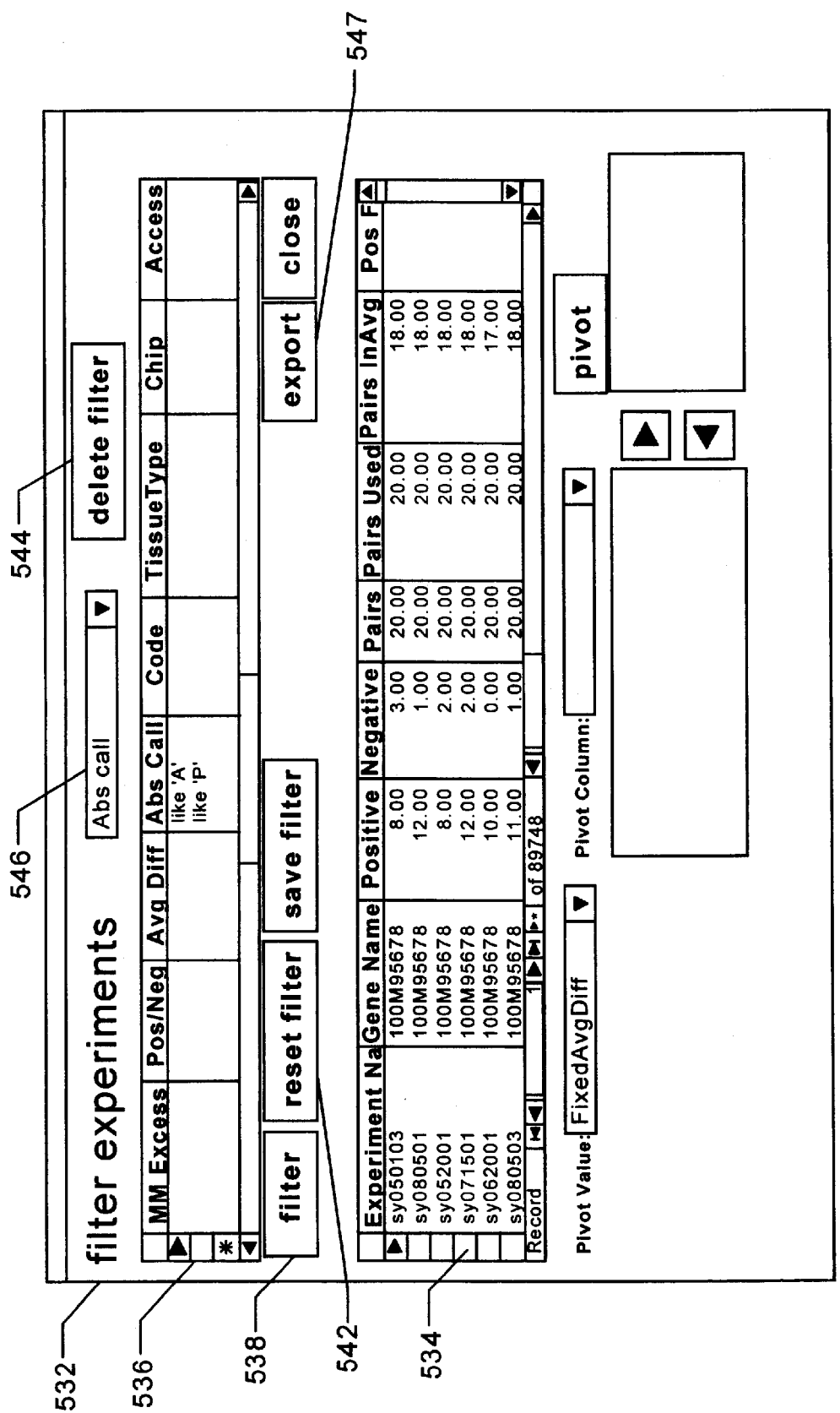

At step 406, the user filters the large set of experimental data that was imported, normalized, and transformed. FIG. 5E depicts a filter experiments form 532. A lower table 534 lists the imported experiments and genes or EST and the expression data associated with each combination of experiment and gene or EST. An upper table 536 is used to enter a query to filter the experiment data in lower table 534. Each column of upper table 536 corresponds to a column in lower column 534. Upper table 536 is similar to a query by example (QBE) grid as included in Microsoft Access. Predicates are entered in the columns of upper table 536 with all the predicates in a single row treated as ANDs and those between rows treated as OR's. The results satisfying a given query are displayed in lower table 534 upon selection of a filter button 538. Filters may be saved, deleted, and reset by use of appropriately labeled buttons, 540, 542, and 544. A stored filter may be loaded by use of a drop-down list 546. Selection of an export button 547 writes the data to an Exel spreadsheet.

Figure 5G:
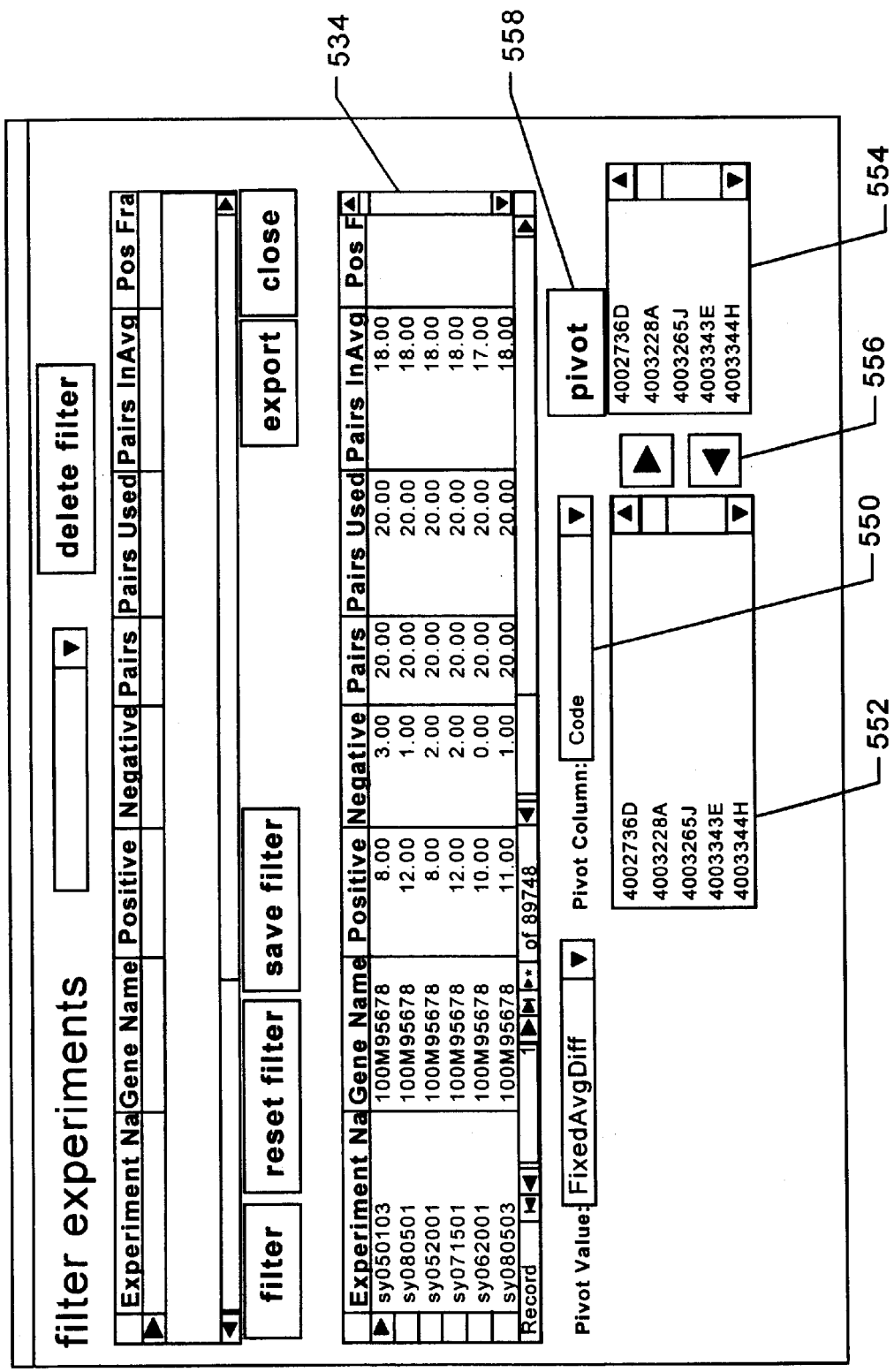

To facilitate further user queries, the user may specify a new field to be used as a pivot field for future queries at step 408. Elements of the selected field will become columns in the new table. FIG. 5F shows how a pivot value is selected by use of a drop-down list 548. The pivot value identifies the expression data that will be listed in the columns of lower table 534. FIG. 5G shows a pivot column drop-down list 550 allows selection of a particular column of lower table 534 as the pivot field. The entries of the selected column are shown in a left list box 552 and moved to a right list box 554 to include them as rows in the pivoted table. The user selects arrow keys 556 to add and delete items of right list box 554. To perform the pivot operation, the user selects a pivot button 558.

Figure 5H:
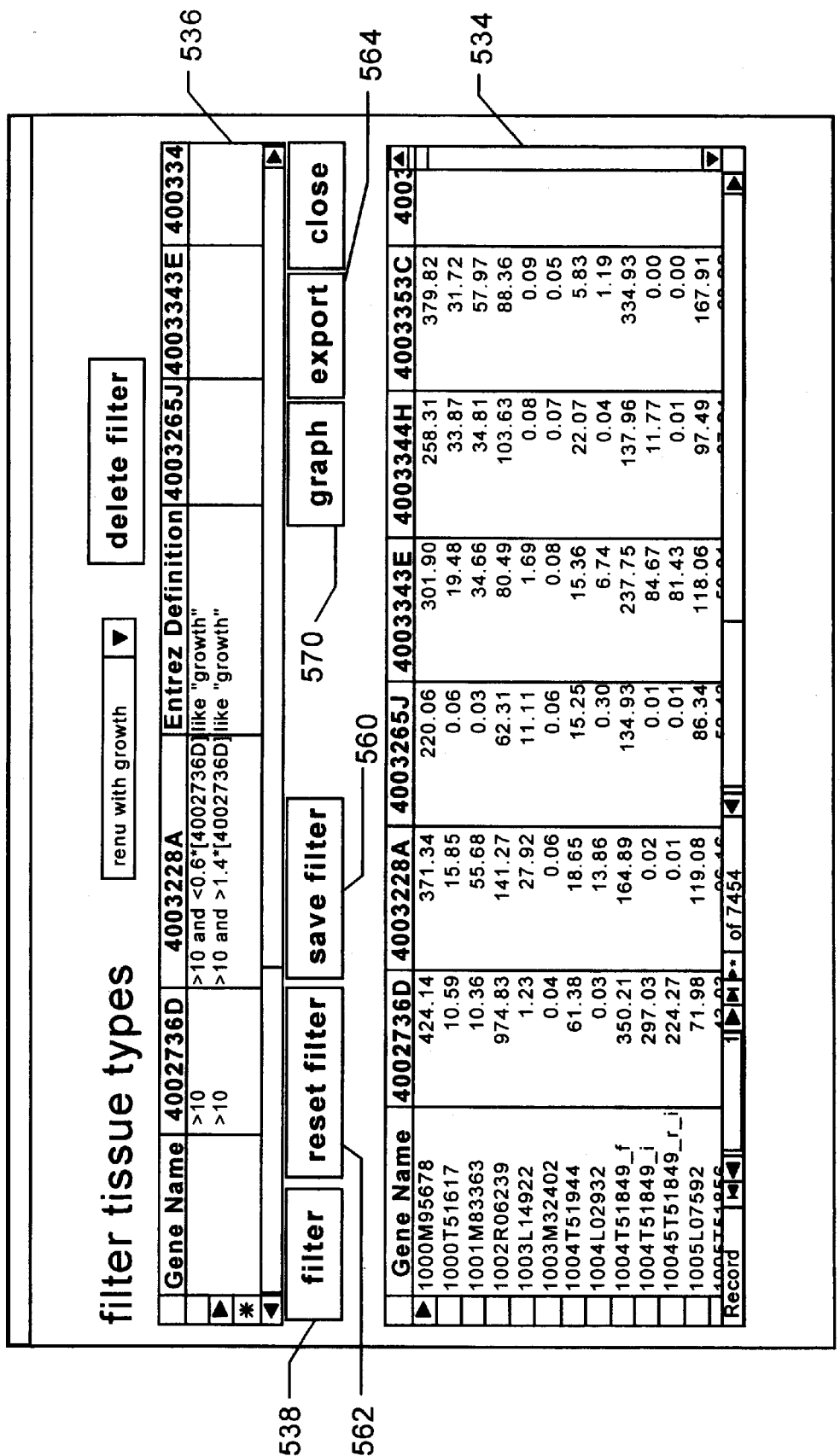

FIG. 5H depicts a user interface for filtering tissue types as displayed as a result of the pivot operation. Lower table 534 shows the result of a pivot operation as described with reference to FIGS. 5F–5G.

Upper table 536 is now used at step 410 to specify a query to filter genes using the results of experiments obtained from different tissue types. Again, predicates in a row are treated as ANDs. Predicates between rows are treated as ORs. By properly formulating a query, the user may answer questions such as which genes are up-regulated in normal tissue and down-regulated in diseased tissue. The depicted Entrez definition column contains the definition column from the public domain Entrez database. The depicted query marked 'like "growth"' retains those records having the string "growth" as a substring in the designated column.

One condition satisfying the depicted query is that a gene have an expression level in experiment 40027366D greater than 10 and an expression level in experiment 4003228A greater than 10 and less than 0.6 times the expression level in experiment 4002736D. An alternate condition satisfying the query is that the expression level in experiment 4002736D be greater than 10 and the expression level in experiment 4003228A greater than 10 and greater than 1.4 times the expression level in experiment 4002736D.

This query determines the genes that have a particular fold change pattern between experiment 4003228A and experiment 4002736D. It will filter out genes for which there is no significant fold change between the experiments. Specifically, it finds all genes for which the expression level of experiment 4003228A is less than 60% of the expression level of experiment 4002736D, or for which the expression level of experiment 4003228A is greater than 140% of the expression level of experiment 4002736D. Both experiments are also constrained to have expression levels greater than 10.

Filters may be saved or reset by selection of buttons 560 and 562, respectively. The records displayed in lower table 534 may be sorted on any column(s), and columns may be hidden, frozen, or repositioned for better viewing. Lower table 534 may also be saved in different formats, including a spreadsheet format such as Microsoft Excel, by clicking on an export button 564. A saved filter may be accessed via a pull down menu 566 or deleted by selection of a delete button 568. Additional information on any gene may be obtained by double clicking its row. This will load an Internet browser program and open a web site such as the Entrez web site that stores information for the gene. The browser program then displays the entry for that gene.

Figure 5I:
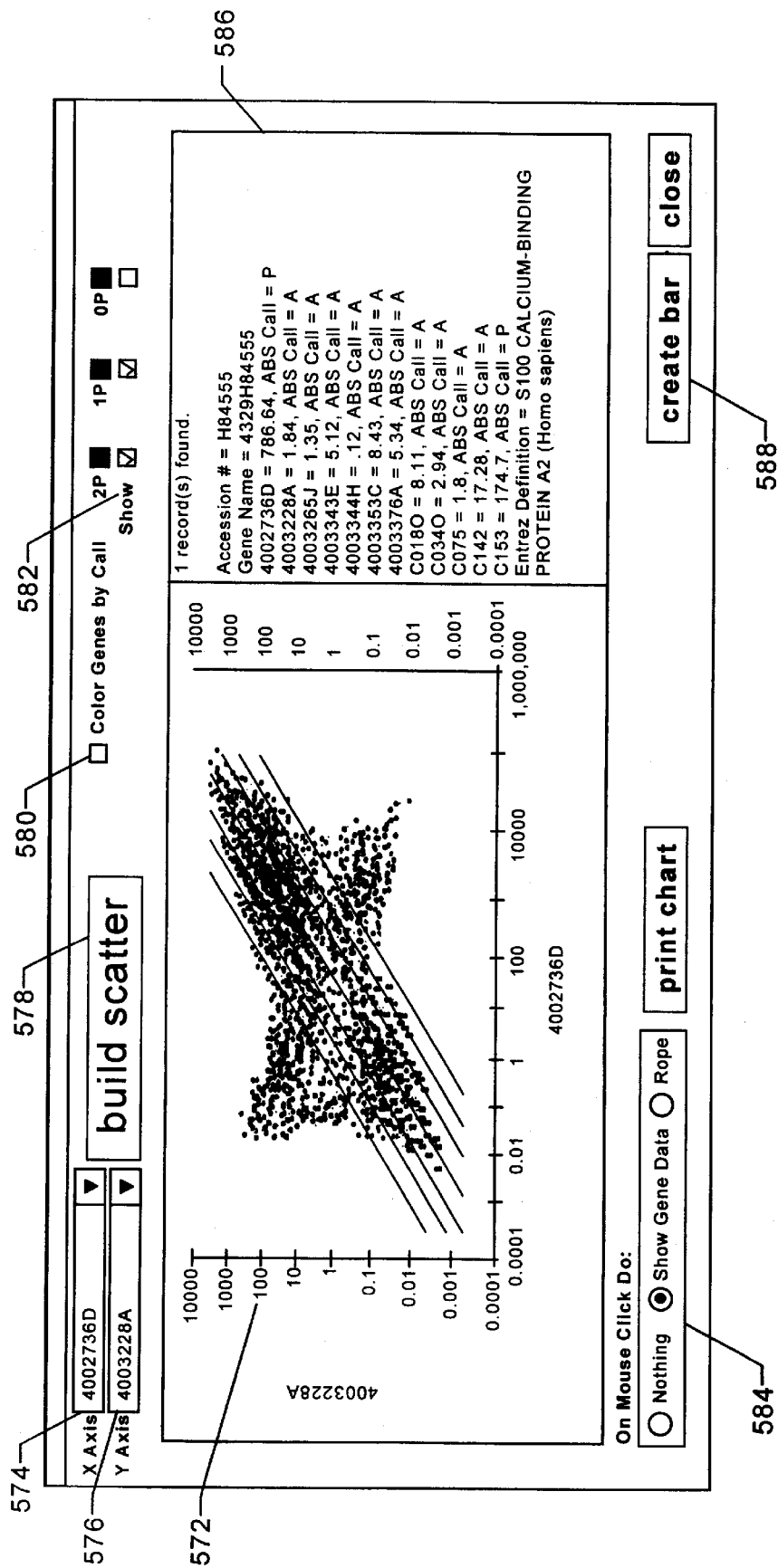

At step 412, by selecting a graph button 570, the user calls up a scatter-plot display 572 depicted in FIG. 5I. Two experiments are selected for comparison using drop-down lists 574 and 576 for the x axis and y axis respectively. The graph is generated by selecting a build scatter button 578. Each point on the scatter plot corresponds to a particular gene. The point is positioned on the graph according to its measured expression level in both experiments. By checking a box 580, the user may select to have the points color coded according to whether the gene was present in both (2P), one (1P), or neither (OP) of the experiments. By checking one or more of boxes 582, the user may elect to show or not show genes according to this categorization.

By making an appropriate selection in a box 584, the user may select an interpretation for future mouse clicks. One choice is for the system to do nothing in response to a mouse click. Another choice is for the system to show gene data for a point selected by a mouse click. The gene data appears in a box 586 including the accession number, the gene name, the expression levels as measured in a variety of experiments, and an expression call for each experiment (either absent or present.) An Entrez definition name is also shown. Double clicking on an entry will invoke an Internet browser to show the Entrez entry for the gene.

The user may also select "rope" in box 584 to collect interesting points for comparison by surrounding them with a polygon. Lines are automatically drawn between each mouse click, encircling those genes to be included in a bar graph. The user may display the bar graph by selecting a button 588.

Figure 5J:
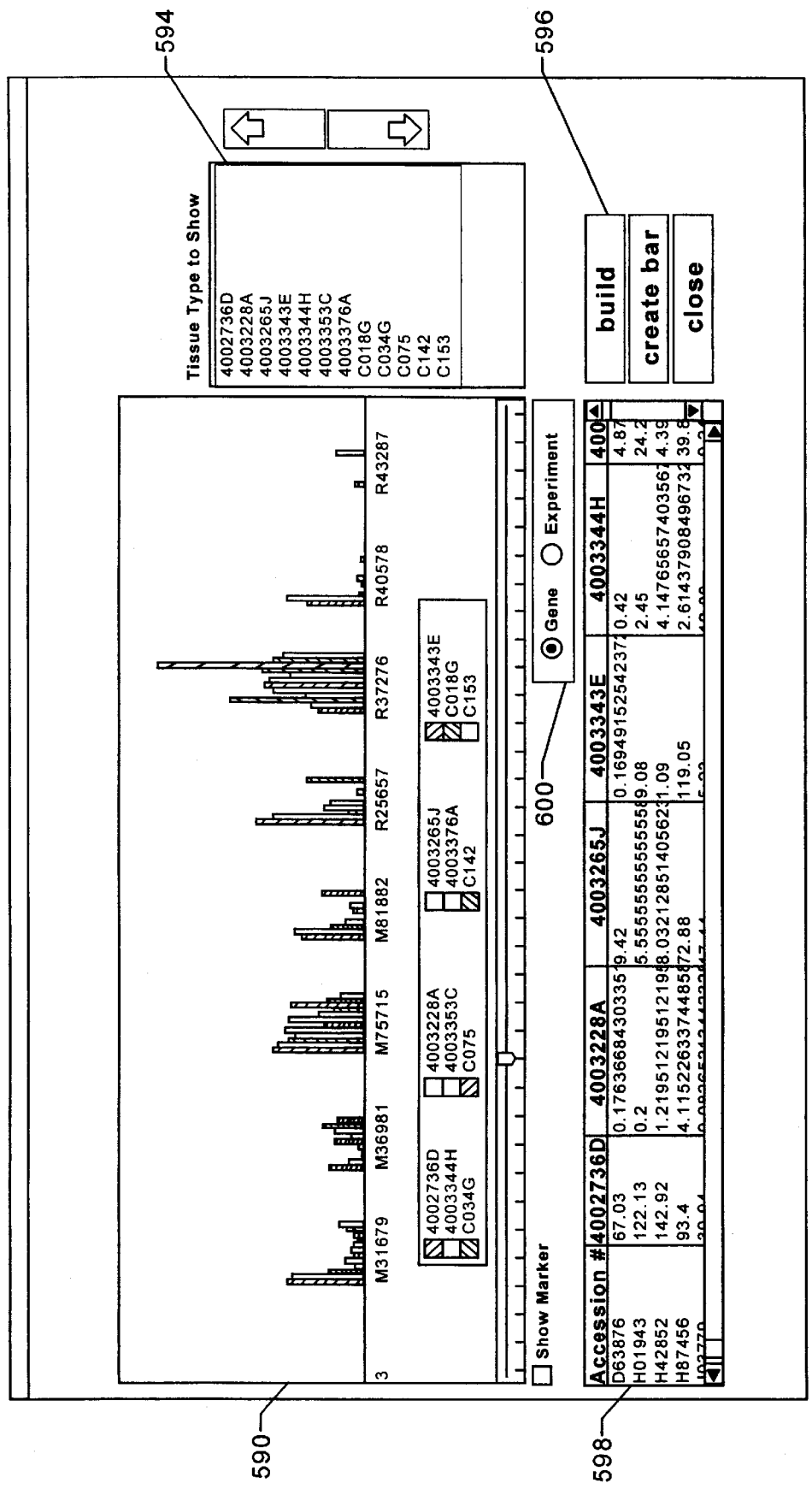

At step 414, FIG. 5J depicts a bar graph 590 for the roped genes in the scatter plot of FIG. 5I. Each grouping of bars in FIG. 5J corresponds to a gene. Each bar within a grouping corresponds to an experiment and is color-coded according to a legend 592. Initially only two experiments are displayed, the two experiments corresponding to the axes of the scatter plot of FIG. 5I. However, the user may select further experiments from a box 594. Once the desired experiments are selected, the user selects a build button 596 to display the desired bar graph. A table 598 shows the expression levels for the depicted genes.

Figure 5K:
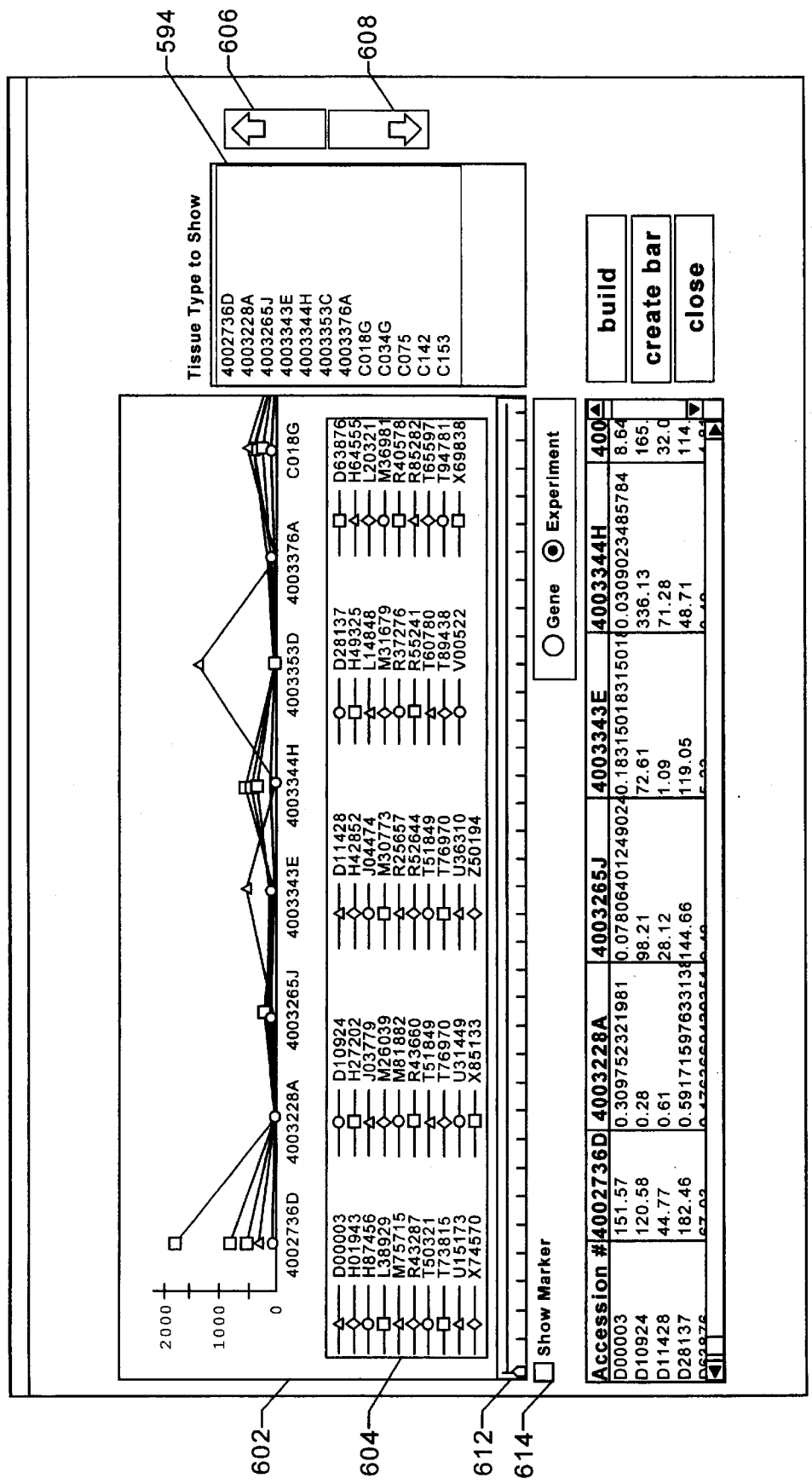

For the display of FIG. 5J, the option "gene" is selected in a box 600. To view individual plots of the expression level for each gene as they vary over the experiments, the user may select option "experiment" in box 600 before selecting build button 596. This produces a line graph 602 as shown in FIG. 5K. The experiments are arranged along the horizontal axis in the order specified in box 594. Each gene has its own trace corresponding to its expression level as it varies over the experiments. A legend 604 identifies the trace for each gene. To change the position of an experiment along the horizontal axis, the user uses up and down arrows 606 and 608 to change its position. This feature makes it possible to reorder the experiments to reflect additional sequencing knowledge. For example, if the experiments represent a time course such as progression of a disease or treatment, they can be graphically ordered in time sequence. The graph then represents the change in expression level as a function of time for the selected gene. A slider icon 612 allows the user to scroll along the horizontal axis if line graph 602 does not fit on the screen. A maker check box 614 shows a horizontal line across line graph 602 defining a particular expression level. This allows the user to easily view data points above the selected level.

Figure 5L:
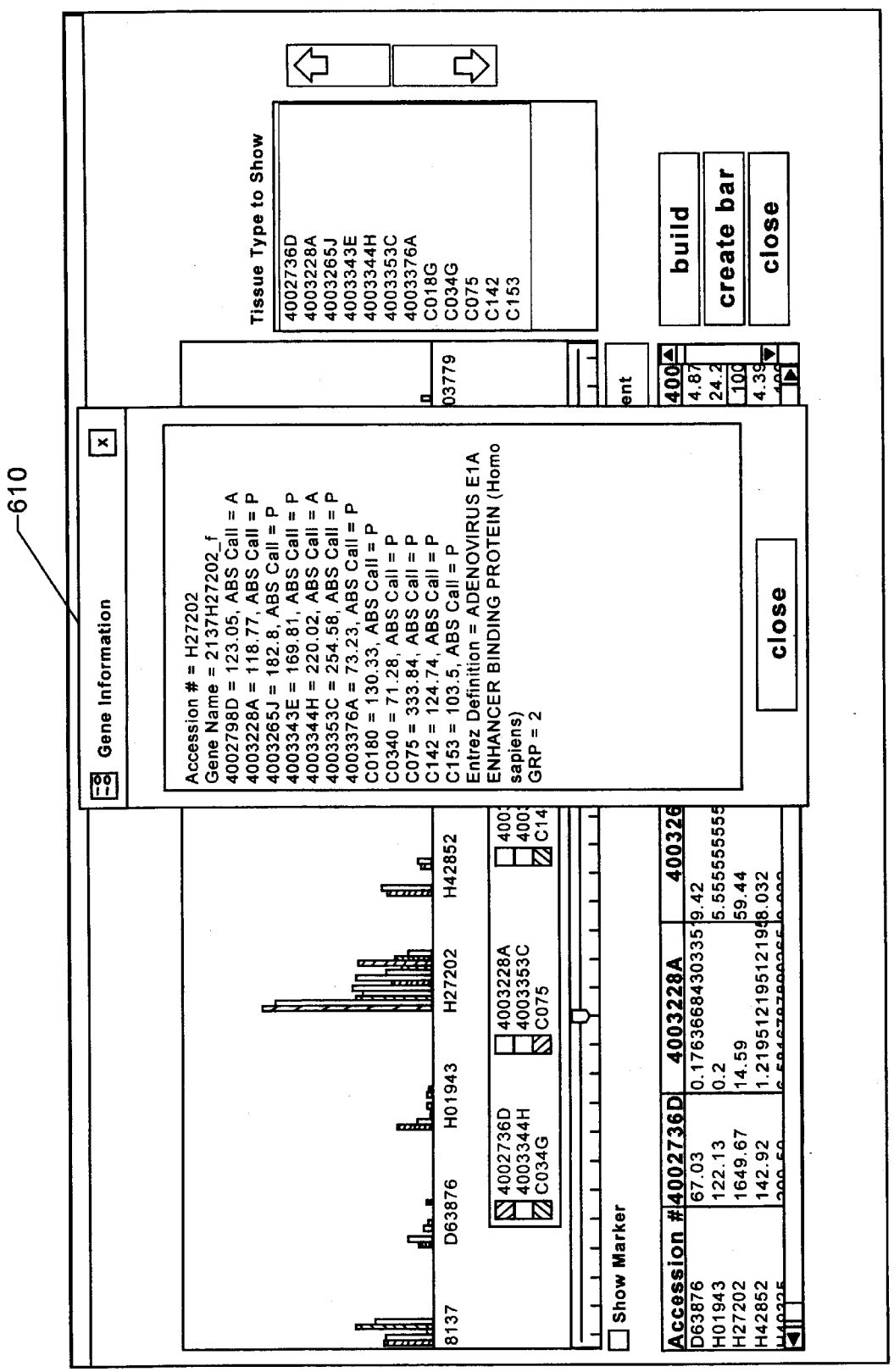

More information about a gene may be obtained by clicking on any bar in the group. All of the information for the gene will be displayed in a separate window 610 as shown in FIG. 5L.

In the foregoing specification, the invention has been described with reference to specific exemplary embodiments thereof. It will, however, be evident that various modifications and changes may be made thereunto without departing from the broader spirit and scope of the invention as set forth in the appended claims and their full scope of equivalents. For example, it will be understood that wherever "expression level" is referred to, one may substitute the measured concentration of any compound. Also, wherever "gene" is referred to, one may substitute the term "expressed sequence tag."

What is claimed is:

1. In a computer system, a method for operating a database storing expression level information comprising:

providing a database comprising expression levels for each of a plurality of genes or expressed sequence tags (EST) as measured in each of a plurality of tissue types;

filtering a plurality of expression levels to obtain a reduced set of expression levels, wherein the step of filtering includes substeps of allowing a user to define a filter table in row and column correspondence to a target table; and applying the filter table to the target table to obtain the reduced set of expression levels;

accepting a user query to said reduced set of expression levels to identify desired ones of said plurality of genes or EST, said user query specifying expression level characteristics of said desired genes; and comparing said expression level characteristics to said expression levels stored in said database to identify said desired genes or EST.

2. The method of claim 1 further comprising:

displaying information identifying said desired genes or EST.

3. The method of claim 1 wherein said plurality of tissue types comprise a diseased tissue type.

4. The method of claim 1 wherein said plurality of tissue types comprise a healthy tissue type.

5. The method of claim 1 wherein said plurality of tissue types comprise a cancerous tissue type.

6. The method of claim 1 wherein said plurality of tissue types comprise a drug treated tissue type.

7. The method of claim 1 wherein said plurality of tissue types comprise issues obtained from disparate species.

8. The method of claim 1 wherein said plurality of tissue types comprise tissues obtained from disparate organs.

9. The method of claim 1 wherein said expression level characteristics comprise expression level ranges as measured for a particular gene in at least two of said plurality of tissue types.

10. The method of claim 1 wherein said expression level characteristics comprise relationships among expression levels as measured for a particular gene in at least two of said plurality of tissue types.

11. The method of claim 1 further comprising:

accepting user input selecting two of said plurality tissue types for graphical display;

displaying a first axis corresponding to a first one of said two tissue types;

displaying a second axis corresponding to a second one of said two tissue types;

for a selected one of said plurality of genes or EST, displaying a mark at a position wherein said position is selected relative to said first axis in accordance with an expression level of said selected gene or EST measured in said first tissue type and selected relative to said second axis in accordance with an expression level of said selected gene or EST measured in said second tissue type.

12. The method of claim 11 further comprising:

repeating said operation of displaying a mark for a plurality of selected genes or EST.

13. In a computer system, a method for operating a database storing information about compound concentration comprising:

providing a database comprising concentrations of a plurality of compounds as measured in a plurality of samples;

filtering a plurality of expression levels to obtain a reduced set of expression levels, wherein the step of filtering includes substeps of allowing a user to define a filter table in row and column correspondence to a target table; and applying the filter table to the target table to obtain the reduced set of expression levels;

accepting a user query to said reduced set of expression levels to identify desired ones of said plurality of compounds, said user query specifying concentration characteristics of said desired compounds in selected ones of said plurality of samples; and comparing said concentration characteristics to said concentrations stored in said database to identify said desired compounds.

14. A computer program product for operating a database storing expression level information comprising:

code that provides a database comprising expression levels for each of a plurality of genes or expressed sequence tags (EST) as measured in each of a plurality of tissue types;

code that filters a plurality of expression levels to obtain a reduced set of expression levels, wherein the step of filtering includes substeps of allowing a user to define a filter table in row and column correspondence to a target table; and applying the filter table to the target table to obtain the reduced set of expression levels;

code that accepts a user query to said reduced set of expression levels to identify desired ones of said plurality of genes or EST, said user query specifying expression level characteristics of said desired genes;

code that compares said expression level characteristics to said expression levels stored in said database to identify said desired genes or EST; and a computer-readable storage medium for storing the codes.

15. The product of claim 14 further comprising:

code that displays information identifying said desired genes or EST.

16. The product of claim 14 wherein said plurality of tissue types comprise a diseased tissue type.

17. The product of claim 14 wherein said plurality of tissue types comprise a healthy tissue type.

18. The product of claim 14 wherein said plurality of tissue types comprise a cancerous tissue type.

19. The product of claim 14 wherein said plurality of tissue types comprise a drug treated tissue type.

20. The product of claim 14 wherein said plurality of tissue types comprise tissues obtained from disparate species.

* * * * *